United States Patent [19]

Chen et al.

[11] Patent Number: 4,575,509

[45] Date of Patent: Mar. 11, 1986

[54] WATER-SOLUBLE FORMULATIONS OF M-AMSA WITH PYROGLUTAMIC ACID

[75] Inventors: Jivn-Ren Chen, Liverpool; Edward C. Shinal, Manlius, both of N.Y.

[73] Assignee: Bristol-Myers Company, New York, N.Y.

[21] Appl. No.: 631,965

[22] Filed: Jul. 18, 1984

Related U.S. Application Data

[63] Continuation of Ser. No. 462,260, Jan. 31, 1983, abandoned, which is a continuation of Ser. No. 386,178, Jun. 8, 1982, abandoned, which is a continuation of Ser. No. 244,928, Mar. 18, 1981, abandoned.

[51] Int. Cl.$^4$ .................... A61K 31/47; C07D 219/10
[52] U.S. Cl. ................................ 514/297; 514/908; 546/106
[58] Field of Search .................. 546/106; 424/257; 514/297

[56] References Cited

U.S. PATENT DOCUMENTS

| | | | |
|---|---|---|---|
| 3,821,403 | 6/1974 | Misato et al. | 514/546 |
| 3,899,585 | 8/1975 | Misato et al. | 514/551 |
| 3,920,814 | 11/1975 | Bocher et al. | 424/115 |
| 3,947,589 | 3/1976 | Misato et al. | 514/563 |
| 4,150,231 | 4/1979 | Ledochowski et al. | 546/106 |
| 4,258,191 | 3/1981 | Dubicki et al. | 546/106 |
| 4,322,424 | 3/1982 | Bouzard et al. | 514/297 |
| 4,335,244 | 6/1982 | Kaplan et al. | 546/106 |
| 4,360,523 | 11/1982 | Kaplan et al. | 514/297 |
| 4,366,318 | 12/1982 | Cain et al. | 546/106 |
| 4,399,283 | 8/1983 | Fisher et al. | 546/106 |

FOREIGN PATENT DOCUMENTS

| | | |
|---|---|---|
| 0035862 | 9/1981 | European Pat. Off. . |
| 0042553 | 12/1981 | European Pat. Off. . |
| 2131404 | 12/1972 | Fed. Rep. of Germany . |
| 50-135212 | 10/1975 | Japan . |
| 1352420 | 5/1974 | United Kingdom . |
| 2076288 | 12/1981 | United Kingdom . |

OTHER PUBLICATIONS

Berge, et al., J. Pharmaceutical Chemistry, Review Article, Pharmaceutical Salts, vol. 666, No. 1, pp. 1–19, Jan. 1977.
Cain, et al., Europ. J. Cancer, vol. 10, pp. 539–549 (1974).
Von Hoff, et al., Cancer Treatment Reports, vol. 62, No. 10, pp. 1421–1426 (10/78).
Legha, et al., Cancer Research, vol. 38, pp. 3712–3716 (12/78).
Provenzano, et al., Arzneim-Forsch./Drug Res. 27(II), No. 8, pp. 1553–1557 (1977).
Selleri, et al., Boll. Chim. Farm., 116, pp. 735–743 (1977).
Saito, et al., Chemical Abstracts, 81, 86747f (1974).
Saito, et al., Chemical Abstracts, 83, 65333u (1975).
Yoshida, et al., Chemical Abstracts, 85, 110386t (1976).
Saito, et al., Chemical Abstracts, 86, 21711y (1977).
Yoshinaga, et al., Chemical Abstracts, vol. 86, 127333s (1977).
Yamada, et al., Chemical Abstracts, 88, 115334w (1978).
Aoki, et al., Chemical Abstracts, 89, 17600f (1978).
Toyoshima, et al., Chemical Abstracts, 90, 66875d (1979).
Takano, Chemical Abstracts, 91, 50986a (1979).
Lachman, et al., ed., The Theory and Practice of Industrial Pharmacy, 2nd., ed. Lee & Febiger, Philadelphia (1976), pp. 503 & 521–524.
Remington's Pharmaceutical Sciences, Osol, et al., editors, Philadelphia College of Pharmacy & Science (1980), pp. 1483–1484.

Primary Examiner—Donald G. Daus
Assistant Examiner—Diana G. Rivers
Attorney, Agent, or Firm—David M. Morse

[57] ABSTRACT

This invention concerns novel water-soluble salts and compositions of the antitumor agent 4'-(9-acridinylamino) methanesulfon-m-anisidide (m-AMSA). More particularly, there are provided (1) the mono- and dipyroglutamate salts of m-AMSA and (2) compositions of m-AMSA with pyroglutamic acid. The novel salts and compositions provided enable m-AMSA to be administered as an aqueous solution without the necessity of using dimethylacetamide as a pharmaceutical vehicle.

11 Claims, 4 Drawing Figures

WATER-SOLUBLE FORMULATIONS OF M-AMSA WITH PYROGLUTAMIC ACID

CROSS-REFERENCE TO RELATED APPLICATIONS

This application is a continuation application of our co-pending prior application Ser. No. 462,260 filed Jan. 31, 1983, now abandoned, which in turn was a continuation of our application Ser. No. 386,178 filed June 8, 1982, now abandoned, which in turn was a continuation of our application Ser. No. 244,928 filed Mar. 18, 1981, now abandoned.

BACKGROUND OF THE INVENTION

1. Field of the Invention

The novel acid addition salts and compositions of the present invention possess the advantageous antitumor properties of the known free base parent compound and in addition have unexpectedly high water-solubility and stability, thus allowing preparation of useful dosage forms for intravenous administration.

2. Description of the Prior Art

The acridine derivative m-AMSA [4'-9-acridinylamino)methanesulfon-m-anisidide] has been reported by Cain, et al. in *Europ. J. Cancer* 10: 539–549 (1974) to possess significant antitumor activity in animal tumor systems. Since then, this compound has been subjected to clinical evaluation with very promising initial results.

When an antitumor agent such as m-AMSA is employed for treating mammalian tumors, it is recognized that stability and solubility of the agent are often the controlling factor in determining route of administration and dosage forms. For instance, a water-soluble substance, as a rule, can be generally administered intravenously whereas a water-insoluble material is limited to other alternative routes of parenteral administration such as intramuscular or subcutaneous requiring solution of the drug in a pharmaceutically acceptable non-aqueous solvent or dispersion in an aqueous solvent system. A therapeutic agent having water solubility also facilitates the absorption of the agent even in nonparenteral dosage forms, i.e. tablets, capsules, etc. Thus, it is decidedly advantageous if a therapeutic agent is water-soluble, particularly when one considers that the most direct route for achieving therapeutic blood levels of a drug is by intravenous administration.

The free base form of m-AMSA has very limited solubility in water and thus cannot be used as a dosage form for intravenous administration. Attempts have been made to prepare acid addition salts to overcome this solubility problem, but the reported monohydrochloride and monomethanesulfonate salts also proved insufficiently water-soluble for practical dosage forms.

The m-AMSA formulation presently in clinical use consists of two sterile liquids which are combined just prior to use. A solution of m-AMSA base in anhydrous N,N-dimethylacetamide is contained in an ampule. A separate vial contains an aqueous lactic acid solution for use as a diluent. When mixed the resulting m-AMSA solution is administered by i.v. infusion.

While the present clinical formulation provides an intravenous dosage form, it suffers from several disadvantages. In addition to the obvious difficulties in preparing and administering the dosage form, it contains dimethylacetamide as a vehicle. Dimethylacetamide has been reported to show various toxic symptoms in animals and may thus prove to be unacceptable or undesirable as a pharmaceutical vehicle.

It is accordingly an object of the present invention to provide water-soluble, stable, therapeutically acceptable forms of m-AMSA which can be administered to mammalian hosts intravenously (as well as by other routes) and which do not contain or require dimethylacetamide as a pharmaceutical vehicle. This object as well as other features and advantages of the invention will be readily apparent to those skilled in the art from the disclosure set out below.

The pyroglutamic acid (2-pyrrolidone-5-carboxylic acid) used as a starting material for the salts of the present invention or as a component of the compositions of the present invention has been reported in U.S. Pat. No. 3,920,814 to potentiate the intrinsic activity and blood levels of certain antibiotics such as penicillin G, penicillin V, ampicillin, cephalothin, gentamycin, tetracycline, etc. That patent also notes that pyroglutamic acid has been reported useful as a medicament for its good psyconormalizing, psychotonic, mood elevating and antitoxic action. Various other patent and literature references disclose pyroglutamate salts including, for example, *Boll. Chim. Farm* 116 (12): 735–743, 1977 (DL-pyroglutamate salt of L-arginine), *Arzneim.-Forsch.* 27 (8): 1553–1557, 1977 (DL-pyroglutamate salt of L-arginine), Japanese Published Patent Application 50/135,212 (DL-2-pyrrolidone-5-carboxylic acid triethanolamine salt as component in pruritis treatment ointment), Japanese Patent No. 74/27,643 (triethanolammonium DL-pyroglutamate as ingredient in shampoo composition), U.S. Pat. No. 3,899,585 (pyroglutamic acid salts of amino acid higher alkyl esters as fungicidal and bactericidal agents; see also U.S. Pat. No. 3,821,403), U.S. Pat. No. 3,947,589 (pyroglutamic acid salts of N-higher aliphatic acyl amino acids for use as fungicidal compositions), Japanese Patent No. 74/14,630 (DL-pyroglutamic acid salts of amino acid alkyl esters for use as fungicides), U.K. Patent No. 1,352,420 (discloses N-cocoyl-L-arginine ethyl ester DL-2-pyrrolidone carboxylate as antimicrobial or germicidal agent; see also West German Published Patent Application No. 2,131,404, Japanese Patent No. 76/22,055, Japanese Patent No. 76/5413, *Oyo Yakuri* 11 (6): 945–953, 1976, *Yukagaku* 25 (7): 404–408, 1976, *Mem. Tokyo Univ. Agric* 20, 51–73, 1978, Japanese Patent No. 78/118,516 and *Nippon Nogei Kagaku Kaishi* 52 (3): 117–121, 1978).

SUMMARY OF THE INVENTION

In one aspect the present invention provides novel water-soluble mono- and di-pyroglutamic acid salts of m-AMSA which upon reconstitution with sterile water or suitable sterile aqueous vehicle can be administered intravenously and which do not have the disadvantages associated with the known intravenous forms of the parent agent.

In another aspect the invention provides stable, solid, water-soluble compositions for reconstitution with water or an aqueous vehicle as stable solutions of m-AMSA, said compositions comprising a mixture of m-AMSA and pyroglutamic acid, the molar ratio of the acid to m-AMSA being from about 1:1 to about 2:1.

Also provided are processes for preparing the abovedescribed salts and compositions.

DETAILED DESCRIPTION

Figure 1:
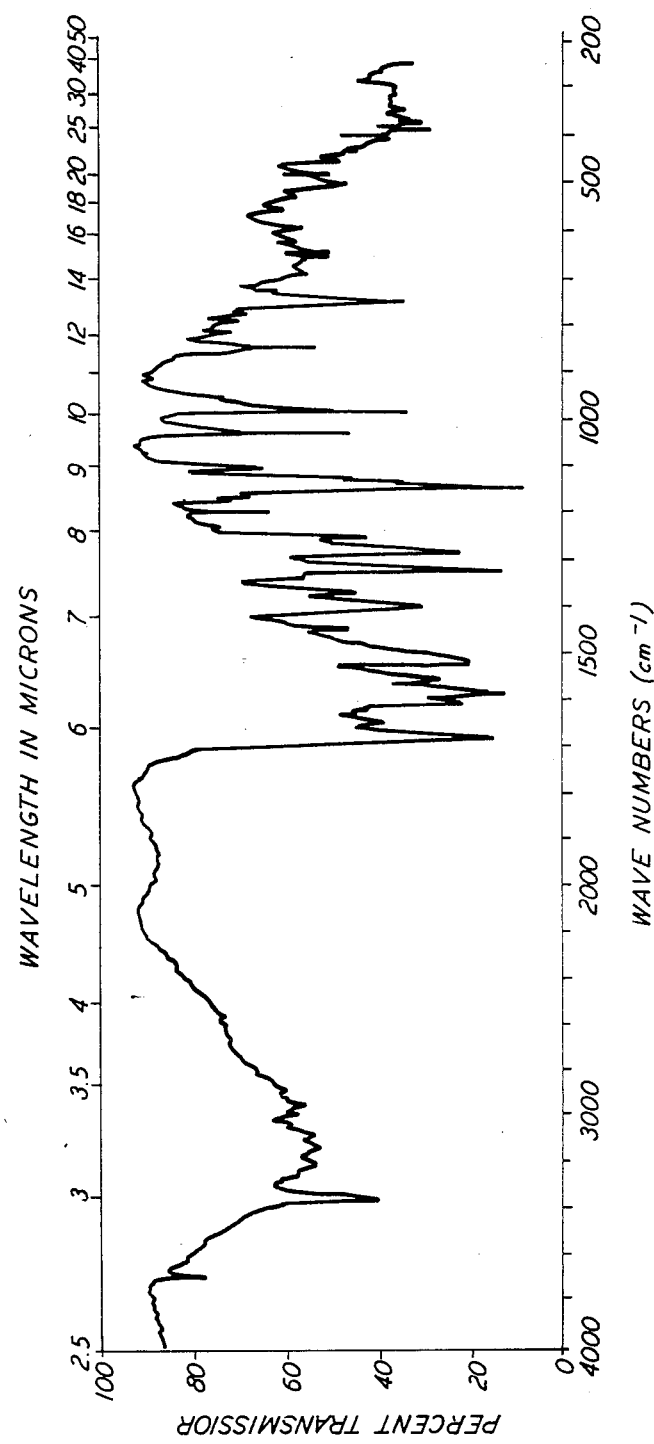
FIG. 1 shows the infrared absorption spectrum of the mono DL-pyroglutamate salt of m-AMSA when pelleted in potassium bromide (Example 1).

Many conventional pharmaceutically acceptable acid addition salts of m-AMSA are only slightly soluble in water and are thus unsuited for preparation of aqueous intravenous solutions. This is evident from literature references to the hydrochloride and methanesulfonate salts as well as from solubility tests carried out by the present inventors on salts such as the levulinate, citrate and lactobionate. While the monomethanesulfonate salt of m-AMSA is reported to be sufficiently soluble for experimental small animal (mice) antitumor studies, the present inventors have found this salt to have an aqueous solubility of about 0.09 mg/ml. which is clearly inadequate for a practical commercial intravenous dosage form.

In investigating solubility properties of m-AMSA acid addition salts, we have unexpectedly found that the salts of m-AMSA and pyroglutamic acid in a molar ratio of 1:1 and 1:2 and physical mixtures of m-AMSA and pyroglutamic acid in a molar ratio of between about 1:1 and 1:2 possess the high desirable solubility, reconstitution and stability properties necessary for a practical intravenous dosage form.

Preparation of the pyroglutamate salts of m-AMSA is accomplished by the steps of
(1) forming a solution of m-AMSA and pyroglutamic acid in an inert organic solvent, the molar ratio of acid to m-AMSA being either about 1:1 or about 2:1, and
(2) recovering the desired m-AMSA mono- or dipyroglutamate salt from the so-produced solution.

Pyroglutamic acid may be obtained in the optically active D- and L-forms or as the optically inactive DL-form. While salts with all of the various forms of pyroglutamic acid appear to be equally advantageous as m-AMSA dosage forms, it is preferred for convenience to use the DL- or L-forms which are most readily available. Most preferably, the DL-acid is employed because of its lower cost relative to the resolved acid forms. For purposes of the present invention, however, all of the various forms of pyroglutamic acid are intended to be included within the scope of the disclosure and claims. The pyroglutamic acid and m-AMSA base are employed in a molar ratio of about 1:1 for preparation of the monopyroglutamate salt and in a molar ratio of about 2:1 for preparation of the dipyroglutamate salt.

The particular inert organic solvent used to solubilize the m-AMSA base and pyroglutamic acid is not critical and examples of suitable solvents will be readily apparent to those skilled in the art. Preferred solvents are polar alcohols and ketones such as methanol, ethanol, n-propanol, isopropanol, acetone, n-butanol, 2-butanone, n-pentanol, n-hexanol, diethylene glycol, methyl isobutyl ketone, 3-pentanone, etc. A particularly preferred solvent is acetone.

The temperature at which solution is effected is not critical and may range from just above the freezing point to just below the boiling point of the solvent system. Most advantageously, temperatures of around room temperature or above are used.

Standard salt recovery techniques such as crystallization or solvent precipitation may be used to obtain the desired m-AMSA salt. After forming the solution of m-AMSA, it is preferable to carry out a filtration step before recovering the solid salt. Seed crystals of the desired salt may be added to the reaction mixture to induce and/or enhance crystallization. After recovery, the salt is washed with an inert organic solvent in which it is substantially insoluble (e.g. methanol or acetone) and dried by conventional procedures. Recrystallization (e.g. from acetone) may be used to obtain product in a highly purified form.

The m-AMSA/pyroglutamic acid physical mixtures (compositions) of the present invention may be employed in the form of either a dry-fill (mixture of dry components) or lyophilized product. The mixtures as in the case of the salts may be conveniently and rapidly reconstituted with water or other sterile aqueous vehicle to provide at least a 5 mg/ml true solution of m-AMSA having excellent stability characteristics.

Preparation of the water-soluble compositions as a dry-fill mixture may be accomplished by simply mixing the appropriate starting materials in the proper proportions. Thus, the m-AMSA base and pyroglutamic acid are mixed in a ratio of from about 1 to 2 moles of pyroglutamic acid per mole of m-AMSA. A preferred embodiment comprises a mixture of about two moles of pyroglutamic acid per mole of m-AMSA.

Preparation of the water-soluble compositions as a lyophilized mixture may be accomplished by subjecting an aqueous solution of the appropriate starting materials in the proper proportions to a standard lyophilization process. Thus, the lyophilized mixture is prepared by forming an aqueous solution of m-AMSA and pyroglutamic acid in a ratio of from about 1 to 2 (preferably about 2) moles of pyroglutamic acid per mole of m-AMSA base and then lyophilizing said aqueous solution to obtain the desired solid composition. Before the lyophilization step, the aqueous solution is preferably filtered to remove any insoluble impurities. Also, conventional excipients such as mannitol may be added to facilitate dissolution of the lyophilized product. Lyophilization may be carried out in conventional laboratory or industrial lyophilizers according to methods well-known to those skilled in the art. Illustrative lyophilization parameters are as follows:

precooling shelves at $-20°$ C.;
freezing at $-40°$ C. for 4 hours;
sublimation at $-45°$ C. with 10 millitor vacuum for 38 hours; and
drying at 30° C. for 38 hours.

The pyroglutamate salts and compositions provided by the present invention exhibit substantially the same antitumor properties as the prior art m-AMSA forms. Because of their high water-solubility, however, they may be used to prepare practical dosage forms for intravenous administration which do not contain an undesirable pharmaceutical vehicle such as dimethylacetamide. The salts and compositions, moreover, can be used to prepare single vial dry-fill or lyophilized product for reconstitution with sterile water or a sterile aqueous vehicle.

The m-AMSA salts and compositions of the present invention may be used to prepare oral or non-intravenous parenteral dosage forms as well as the preferred intravenous injectable product. The salts and compositions, both in solid form and in aqueous solution, have acceptable stability for viable pharmaceutical dosage forms.

In the treatment of mammalian tumors, the salts and compositions of the present invention may be administered either orally or parenterally, but preferably parenterally, in dosages (adjusted for amount of m-AMSA base) and according to regimens previously disclosed in the literature. A suggested dosage range of m-AMSA base in a unit dosage form is from about 20–200 milligrams.

The following examples are given in illustration of, but not in limitation of, the present invention.

EXAMPLE 1

Preparation of m-AMSA Mono DL-Pyroglutamate Salt

DL-Pyroglutamic acid (130 mg) was dispersed in 20 ml of acetone to form a solution. To this solution there was added 400 mg of m-AMSA free base. The mixture was stirred and 10 ml of methyl alcohol added drop by drop. Upon agitation, a yellow solid gradually precipitated. The precipitate was collected, washed twice with acetone and dried in vacuo to give the title salt having a melting point of 156°–158° C. and an aqueous solubility at room temperature of about 10 mg/ml.

FIG. 1 shows the infrared absorption spectrum of the mono DL-pyroglutamate salt when pelleted in potassium bromide.

Figure 2:
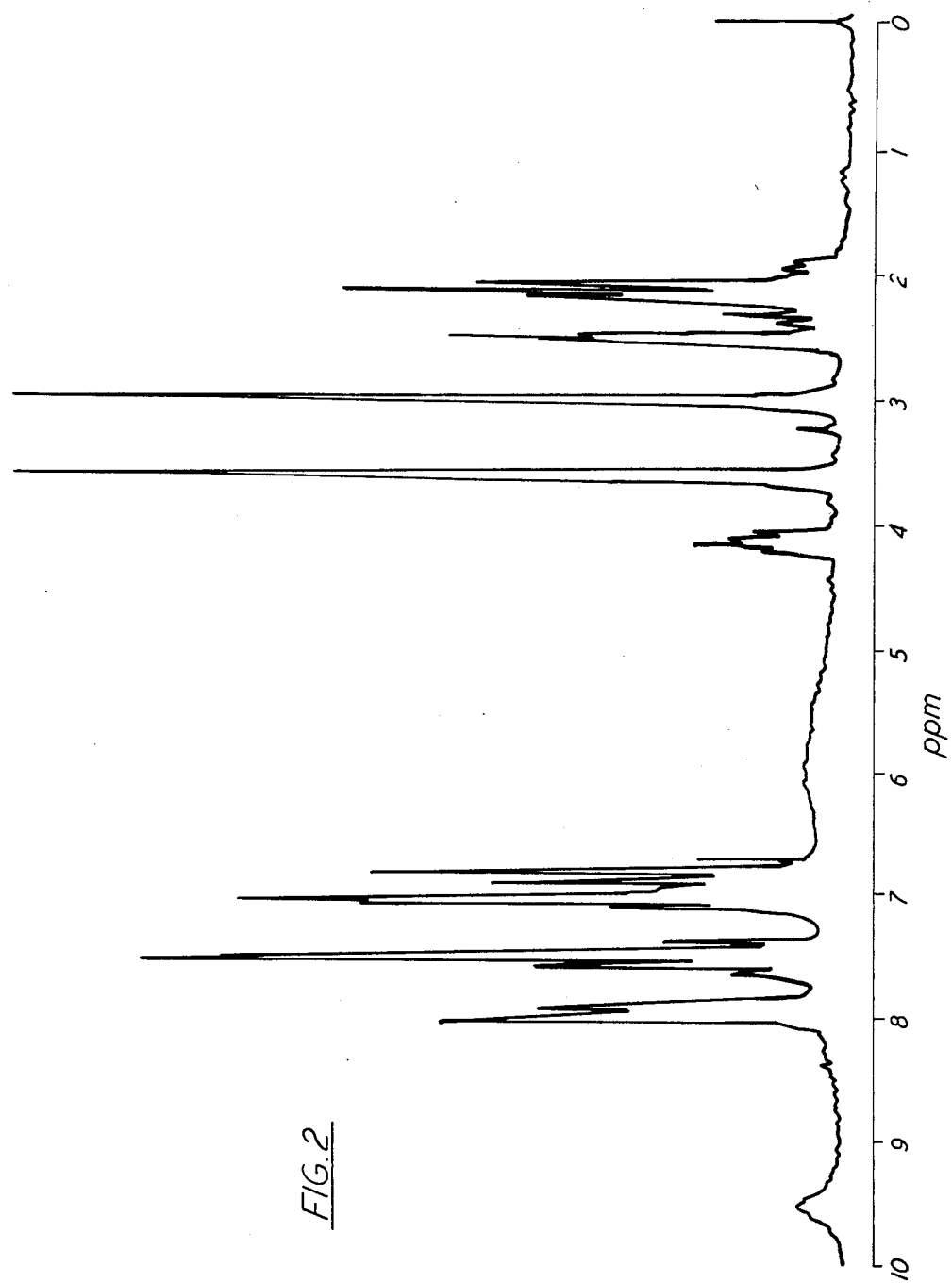
FIG. 2 shows the nuclear magnetic resonance spectrum of the mono DL-pyroglutamate salt of m-AMSA dissolved in dimethylsulfoxide (Example 1).

FIG. 2 shows the nuclear magnetic resonance spectrum of the mono DL-pyroglutamate salt dissolved in dimethylsulfoxide. The nmr spectrum is consistent for a mono salt.

The ultraviolet absorption spectrum of the product salt (dissolved in water at a concentration of 0.01024 g/l) showed the following $\lambda_{max}$ and absorptivities:

| $\lambda_{max}$, nm | Absorptivity, a |
|---|---|
| 434 | 26.2 |
| 263 | 106.2 |
| 243 | 70.3 |
| 204 | 109.4 |

Elemental analysis of the product salt gave the following % values:

Calculated: C, 59.81; H, 4.98; N, 10.73; S, 6.14.
Found: C, 58.32; H, 4.91; N, 11.32; S, 5.94; H₂O(KF), 1.93.

EXAMPLE 2

Preparation of m-AMSA Di DL-Pyroglutamate Salt m-AMSA base (400 mg) was suspended in 30 ml of dried acetone. With gentle stirring, a solution was obtained by gradually adding a solution of 260 mg of DL-pyroglutamic acid in 15 ml of methanol to the above suspension. Two 10 ml portions of dried methanol were added to the solution to precipitate the dipyroglutamate salt. The salt was isolated by filtration, washed with methanol and dried in a vacuum dessicator. The yield of dipyroglutamate salt was about 600 mg; mp 145°–148° C. The salt gave an aqueous solubility (m-AMSA base content as determined by HPLC) of 13.1 mg/mg.

Figure 3:
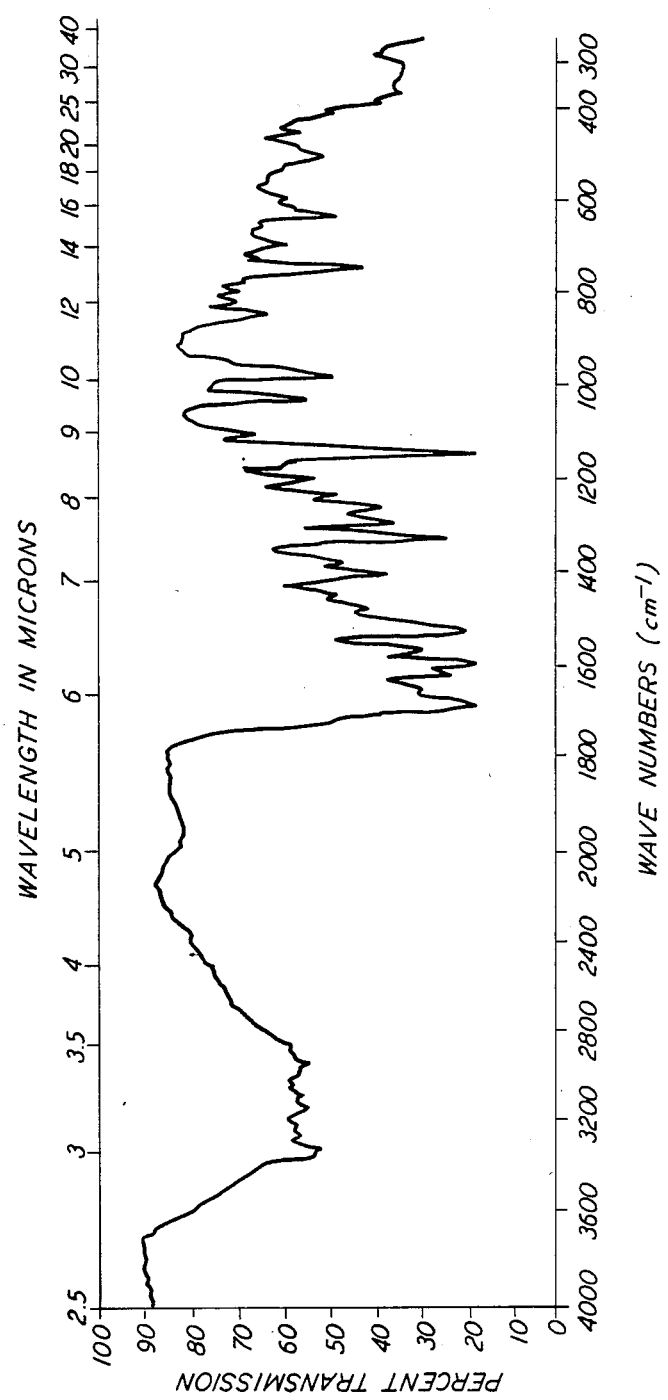
FIG. 3 shows the infrared absorption spectrum of the di DL-pyroglutamate salt of m-AMSA when pelleted in potassium bromide (Example 2).

FIG. 3 shows the infrared absorption spectrum of the di DL-pyroglutamate salt when pelleted in potassium bromide.

Figure 4:
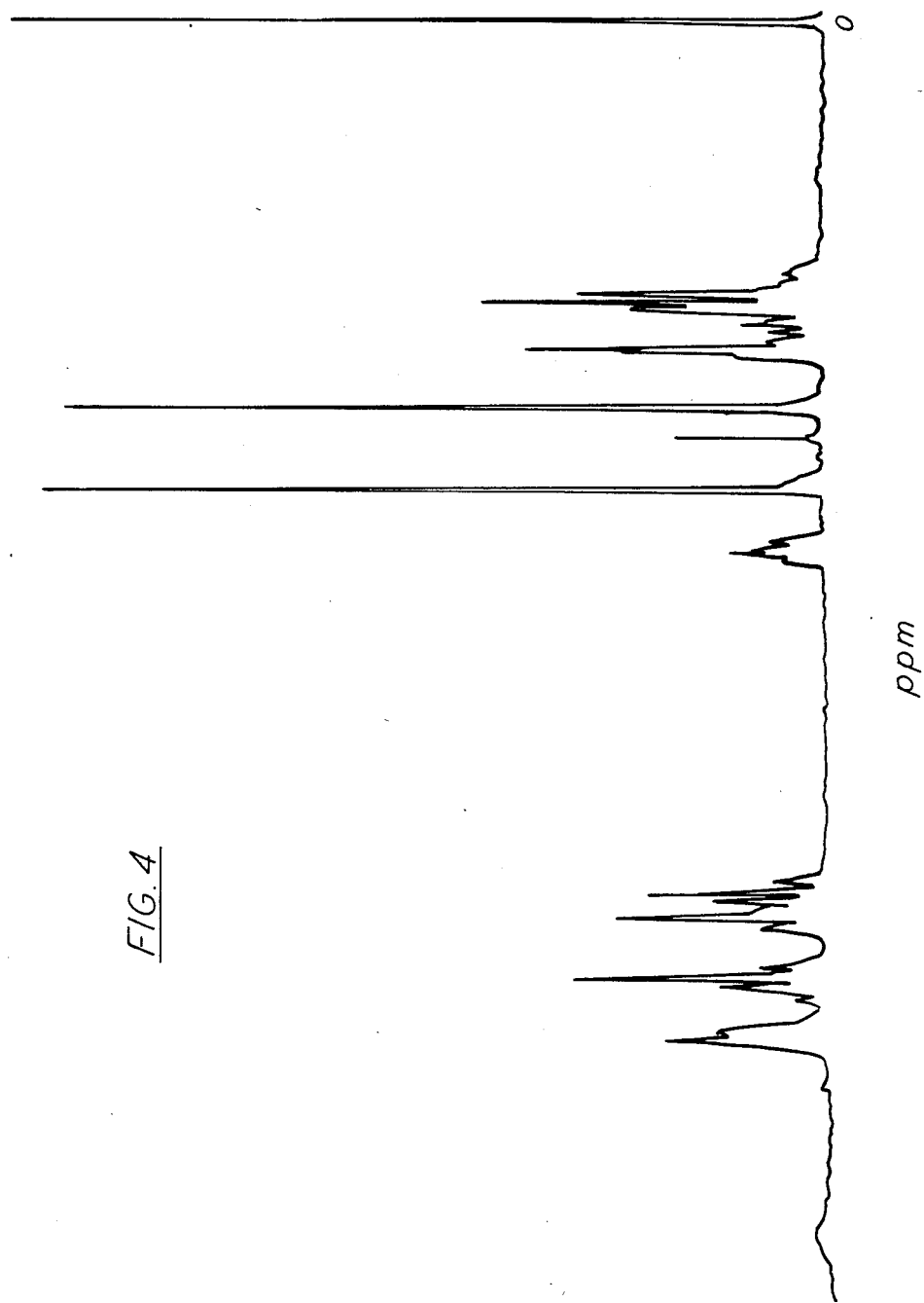
FIG. 4 shows the nuclear magnetic resonance spectrum of the di DL-pyroglutamate salt of m-AMSA dissolved in dimethylsulfoxide (Example 2).

FIG. 4 shows the nuclear magnetic resonance spectrum of the di DL-pyroglutamate salt dissolved in dimethylsulfoxide.

The ultraviolet absorption spectrum of the product salt (dissolved in water at a concentration of 0.0135 g/l) showed the following $\lambda_{max}$ and absorptivities:

| $\lambda_{max}$, nm | Absorptivity, a |
|---|---|
| 434 | 17.8 |
| 264 | 71.1 |
| 244 | 47.3 |
| 205 | 69.6 |

Elemental analysis of the product salt gave the following % values:

Calculated: C, 57.13; H, 5.06; N, 10.74; S, 4.92.
Found: C, 56.06; H, 5.06; N, 11.37; S, 5.01; H₂O(KF), 1.86.

EXAMPLE 3

Lyophilized Mixture of m-AMSA and DL-Pyroglutamic Acid (1:2)

A solution was prepared of DL-pyroglutamic acid (258.22 mg; 0.002 moles) in 70.0 ml of sterile water for injection. With gentle stirring, m-AMSA base (393.5 mg; 0.001 mole) was dissolved in the aqueous solution. The aqueous solution of m-AMSA and acid was then made up to 78.7 ml of total volume. Ten ml portions of this solution were then added to 15 ml flint glass vials (8 vials were obtained; one vial contained only 8.5 ml of solution). Butyl lyophilization stoppers were partially inserted into the vials and the stoppered vials then lyophilized according to the following parameters:

prefreezing at −20° C.;
freezing at −40° C. for 4 hours;
sublimation at −45° C. with 10 millitorr vacuum for 38 hours; and
drying at 30° C. for 38 hours.

A yellow sponge-like cake was obtained. Upon reconstitution of the lyophilized product with 10 ml of sterile water for injection, a complete solution resulted. An HPLC assay of the lyophilized product showed a 95.11% purity.

EXAMPLE 4

Lyophilized Mixture of m-AMSA and DL-Pyroglutamic Acid (1:1)

If the general procedure of Example 3 is repeated with a 1:1 molar ratio of m-AMSA base and DL-pyroglutamic acid, the title 1:1 lyophilized mixture is obtained.

EXAMPLE 5

Preparation of m-AMSA Mono L-Pyroglutamate Salt

If the general procedure of Example 1 is repeated with the DL-pyroglutamic acid replaced by an equimolar amount of L-pyroglutamic acid, there is obtained the title salt.

EXAMPLE 6

Preparation of m-AMSA Di L-Pyroglutamate Salt

If the general procedure of Example 2 is repeated with the DL-pyroglutamic acid replaced by two molar equivalents of L-pyroglutamic acid, there is obtained the title salt.

EXAMPLE 7

Preparation of m-AMSA Di D-Pyroglutamate Salt

If the general procedure of Example 2 is repeated with the DL-pyroglutamic acid replaced by two molar equivalents of D-pyroglutamic acid, there is obtained the title salt.

EXAMPLE 8

Preparation of m-AMSA Mono D-Pyroglutamate Salt

If the general procedure of Example 1 is repeated with the DL-pyroglutamic acid replaced by an equimolar amount of D-pyroglutamic acid, there is obtained the title salt.

EXAMPLE 9

Lyophilized Mixture of m-AMSA and L-Pyroglutamic Acid (1:1)

If the general procedure of Example 4 is repeated with the DL-pyroglutamic acid used therein replaced by an equimolar amount of L-pyroglutamic acid, there is obtained the title 1:1 lyophilized mixture.

EXAMPLE 10

Lyophilized Mixture of m-AMSA and L-Pyroglutamic Acid (1:2)

If the general procedure of Example 3 is repeated with the DL-pyroglutamic acid used therein replaced by two molar equivalents of L-pyroglutamic acid, there is obtained the title 1:2 lyophilized mixture.

EXAMPLE 11

Dry-fill Mixture of m-AMSA and L-Pyroglutamic Acid (1:1)

| Ingredient | Formula Per Vial |
|---|---|
| Sterile m-AMSA base, 60 mesh | *50 mg of m-AMSA activity |
| L-pyroglutamic acid, 60 mesh | 1 molar equivalent |

*actual amount used dependent on potency

PROCEDURE

Using aseptic technique, place the required amounts of sterile 60 mesh m-AMSA base and L-pyroglutamic acid in a sterile blender. After blending for 2 hours, the blend is assayed and, using aseptic technique, added to sterial vials. Vials are capped with sterile rubber enclosures and sealed with aluminum seals.

EXAMPLE 12

Dry-fill Mixture of m-AMSA and DL-Pyroglutamic Acid (1:1)

If the general procedure of Example 11 is repeated with the L-pyroglutamic acid used therein replaced by an equimolar amount of DL-pyroglutamic acid, the title 1:1 dry-fill mixture is obtained.

EXAMPLE 13

Dry-fill Mixture of m-AMSA and DL-Pyroglutamic Acid (1:2)

If the general procedure of Example 12 is repeated using 2 molar equivalents of DL-pyroglutamic acid, there is obtained the title 1:2 dry-fill mixture.

SOLUBILITY TESTING

To determine the relative solubilities of the pyroglutamate salts and compositions of the present invention and the prior art m-AMSA methanesulfonate salt, the following solubility test was carried out.

PROCEDURE

The following formulations were tested:
(1) m-AMSA methanesulfonate salt (1:1 molar ratio);
(2) a composition of m-AMSA and methanesulfonic acid in a ratio of 2 moles methanesulfonic acid per mole of m-AMSA base;
(3) m-AMSA DL-pyroglutamate salt (1:1 molar ratio); and
(4) m-AMSA DL-pyroglutamate salt (1:2 molar ratio).

The formulations were prepared as follows:
(1) The m-AMSA methanesulfonate salt was prepared by slurrying 1 g of m-AMSA base in 125 ml of acetone for 20 minutes. The resulting near solution was vacuum filtered to remove undissolved solids. The solids remaining in the filter were washed with 10 ml of acetone and the wash solution was added to the original filtrate. To the above solution of m-AMSA base there was added with rapid stirring 0.24 ml of methanesulfonic acid over a three minute interval. Crystals formed and the mixture was stirred five additional minutes. The crystals were then vacuum filtered, washed with two 20 ml portions of acetone and vacuum dried at 50° C. for 24 hours to give 1.18 g of m-AMSA methanesulfonate (1:1) salt.
(2) The composition containing m-AMSA base and methanesulfonic acid (1:2 ratio) was prepared by adding 1 equivalent of methanesulfonic acid to the 1:1 m-AMSA methanesulfonate salt prepared above.
(3) The 1:1 m-AMSA pyroglutamate salt was prepared as described in Example 1.
(4) The 1:2 m-AMSA pyroglutamate salt was prepared as described in Example 2.

To carry out the solubility test, accurately weighed amounts of the above-described formulations were added into accurately measure amounts of sterile water for injection and the mixture was shaken by Vortex ® mixer for 5 minutes to yield a complete solution. The procedure was continued until no more material dissolved in the solution. The saturated solutions were then passed through a 0.22μ Millipore ® filter. The resultant clear filtrates were sampled and assayed via HPLC assay within one hour after reconstitution. Solubility was measured as the m-AMSA base content in the filtrate.

| Results | |
|---|---|
| Formulation | Solubility (mg/ml m-AMSA base) |
| (1) m-AMSA methanesulfonate salt (1:1) | 0.090 |

-continued

| Formulation | Results Solubility (mg/ml m-AMSA base) |
|---|---|
| (2) m-AMSA base and methanesulfonic acid (1:2) | 0.082 |
| (3) m-AMSA pyroglutamate salt (1:1) | 12.5 |
| (4) m-AMSA pyroglutamate salt (1:2) | 13.1 |

We claim:

1. The mono DL-pyroglutamate salt of m-AMSA.
2. The mono D-pyroglutamate salt of m-AMSA.
3. The mono L-pyroglutamate salt of m-AMSA.
4. The DL-pyroglutamate salt of m-AMSA.
5. The D-pyroglutamate salt of m-AMSA.
6. The L-pyroglutamate salt of m-AMSA.
7. A stable, solid, water-soluble composition for reconstitution with water or aqueous vehicle as a stable solution of m-AMSA, said composition comprising a mixture of about one to two moles of pyroglutamic acid per mole of m-AMSA.
8. The composition according to claim 7 wherein the pyroglutamic acid and m-AMSA are in a molar ratio of about 2:1, respectively.
9. The composition according to claim 7 or claim 8 wherein the pyroglutamic acid is DL-pyroglutamic acid.
10. The composition according to claim 7 or claim 8 wherein the pyroglutamic acid is L-pyroglutamic acid.
11. The composition according to claim 7 or claim 8 wherein the pyroglutamic acid is D-pyroglutamic acid.

* * * * *